United States Patent [19]

Castel

[11] Patent Number: 4,535,777
[45] Date of Patent: Aug. 20, 1985

[54] METHOD OF PROVIDING ELECTRICAL STIMULATION OF TISSUE

[75] Inventor: John C. Castel, Lake Bluff, Ill.

[73] Assignee: Physio Technology, Inc., Topeka, Kans.

[21] Appl. No.: 656,403

[22] Filed: Sep. 28, 1984

Related U.S. Application Data

[63] Continuation of Ser. No. 294,715, Aug. 20, 1981, abandoned.

[51] Int. Cl.³ ............................................. A61N 1/36
[52] U.S. Cl. .................................................. 128/421
[58] Field of Search ................ 128/419 R, 420 R, 421, 128/422, 423 R

[56] References Cited

U.S. PATENT DOCUMENTS

| | | | |
|---|---|---|---|
| 2,350,797 | 6/1944 | Morland et al. | 128/421 |
| 3,384,090 | 5/1968 | Manfredi | 128/422 |
| 3,794,022 | 2/1974 | Nawracaj et al. | 128/422 |
| 4,102,348 | 7/1978 | Hihard et al. | 128/422 |
| 4,177,819 | 12/1979 | Kofsky | 128/422 |
| 4,210,151 | 7/1980 | Keller, Jr. | 128/421 |
| 4,237,899 | 12/1980 | Hagfors et al. | 128/422 |

OTHER PUBLICATIONS

Haas, "Radio-Electronics", Dec. 1956, pp. 53–55.

*Primary Examiner*—William E. Kamm
*Attorney, Agent, or Firm*—Wood, Dalton, Phillips, Mason & Rowe

[57] ABSTRACT

An electrotherapeutic method of providing electrical stimulation to human or animal tissue. A stimulating pulse train, having a primary frequency of 500 Hz to 100,000 Hz, is coupled to two electrodes attached to the portion of tissue to be stimulated. The train of pulses of the primary frequency are gated on and off so that they are applied and discontinued in predetermined intervals. For neural stimulation, the gating is performed at 0.1 Hz to 200 Hz. For muscle stimulation, the current is provided for predetermined intervals of 0.001 to 100 seconds and is discontinued in alternate intervals for 0.001 to 100 seconds. The stimulating pulse train may be amplitude modulated so that its amplitude rises at the beginning of each on-time period and falls at the end of each on-time period, the rise and fall time varying between 0.5% and 50% of the total on-time of the stimulating current.

25 Claims, 6 Drawing Figures

METHOD OF PROVIDING ELECTRICAL STIMULATION OF TISSUE

This application is a continuation of application Ser. No. 294,715, filed Aug. 20, 1981, now abandoned.

BACKGROUND OF THE INVENTION

The present invention relates to an electronic stimulating apparatus, and more specifically, to modulated electronic stimulating apparatus and techniques for providing intermittent pulse trains for pain and muscle treatment.

Electrical stimulation of nerves, muscles, and other tissue for medical purposes has been well-known in the prior art for some time. Various devices and techniques have been used in attempts to provide the optimum treatment for pain and other tissue stimulation. In a variety of these techniques, low-frequency currents have been used to produce the desired stimulus. The low frequencies have been generated individually as well as by the interference of several medium frequency currents to produce low-frequency beat currents. The low-frequency stimulation, whether by direct application of frequencies in the range of 1 to 500 Hz, or by creation of beat frequencies in the range of 1 to 100 Hz have been observed to have direct stimulating effects on nerves and muscles. Nevertheless, the effects produced by the low-frequency stimulation are not always desirable for treating nerves and muscles under all circumstances.

In other techniques and apparatus of the prior art, it is known to use frequencies in the range of 2,000 to 3,000 Hz for stimulating the muscles of a patient. In U.S. Pat. No. 4,177,819, for example, a 2,000 to 3,000 Hz signal is modulated in bursts of 40 to 60 Hz and provided in intervals of 2 to 20 second periods separated by 2 to 50 second rest intervals. Again, while this system and technique provides for muscle stimulation and allegedly overcomes disadvantages of pain, discomfort and skin burns, the technique does not provide certain desirable effects that are necessary in the treatment of neurofibers and muscle stimulation.

In addition to the above devices, there are known high-frequency electrode devices which are used in cutting and burning of tissue for surgical and other medical purposes. Such devices operate in the frequency range of in excess of one megacycle and are modulated in a variety of ways to produce cutting and burning of animal tissue. These devices are not used for muscle stimulation and the teachings with respect to their high-frequency operation are generally not applicable to the techniques and systems used for pain and muscle control.

Accordingly, there is a present need for improved apparatus and techniques which produce desirable effects for nerve and muscle stimulation. The present invention has therefore been developed to overcome the specific shortcomings of the above known and similar techniques and to provide an electronic apparatus and technique for providing high-frequency pulsed nerve and muscle stimulation.

SUMMARY OF THE INVENTION

The present invention includes a system and technique for providing high-frequency stimulation of nerves and muscle tissue. The device includes a pulse generator which produces a high frequency in the range of 500 to 100,000 Hz which is coupled to an output amplifier for application of the pulses at a predetermined level to electrodes attached to living tissue. A gate control is coupled to provide a variable gating signal which is capable of turning the pulse generator on and off for periods of 0.1 to 100 seconds and alternatively at frequencies of 0.1 Hz to 200 Hz with duty cycles of 10% to 90%. A ramp generator may be connected to the output amplifier to provide an amplitude control for the output pulses from the pulse generator so that at the beginning of each on period, the pulses gradually increase from zero to their predetermined level and at the end of each on period, the pulses gradually decrease from their preset level to zero. The ramp generator is constructed so that the ramp time varies between 0.5% and 50% of the gate on-time of the high-frequency pulses.

It is therefore a feature of the invention to provide an electronic stimulating system and technique which provides high-frequency signals for tissue stimulation.

It is another feature of the invention to provide a tissue stimulating system and technique which provides high-frequency signals for predetermined periods separated by alternate periods where the high-frequency signals are terminated.

It is another feature of the invention to provide a tissue stimulating apparatus and technique wherein the amplitude of the high-frequency stimulating signals is varied in accordance with a predetermined ramp signal.

Still another feature of the invention is to provide a high-frequency apparatus and technique wherein the high frequency is gated to provide alternate on/off periods at frequencies in the range of 0.1 Hz–200 Hz with a duty cycle of 10% to 90%.

Yet another feature of the invention is to provide a tissue stimulating apparatus and technique which employs high-frequency signals having an amplitude controlled by a ramp function varying from 0.5% to 50% of the on-time of the high-frequency pulses.

These and other novel features of the present invention will become apparent from the following detailed description of the invention when taken with the accompanying drawings wherein:

BRIEF DESCRIPTION OF THE DRAWINGS

FIG. 1a is a schematic diagram showing a typical high-frequency sine waveform used in accordance with the present invention.

FIG. 1b is a schematic diagram showing the square wave gating signal used to control the waveform of FIG. 1a.

FIG. 1c is a schematic diagram showing the ramp waveform used to control the amplitude of the high-frequency waveform of FIG. 1a.

FIG. 1d is a schematic diagram showing the high-frequency pulse waveform produced by the gating and ramp functions of FIG. 1b and FIG. 1c to produce an output current for tissue stimulation in accordance with the present invention.

FIG. 1e is a schematic diagram showing a frequency-modulated waveform as used herein.

FIG. 2 is a block diagram of the apparatus for producing the high-frequency stimulation in accordance with the present invention.

DETAILED DESCRIPTION OF A PREFERRED EMBODIMENT

Figures 1A, 1B, 1C, 1D, 1E, 2:
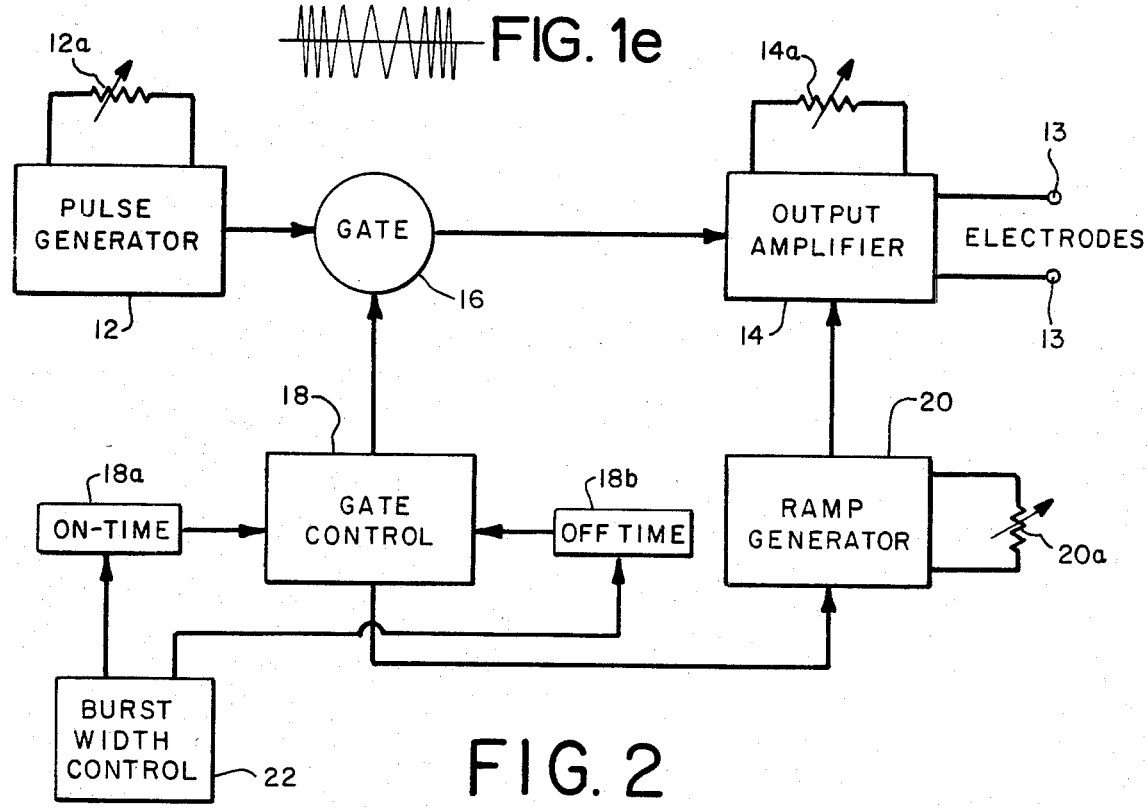

As has been noted previously, prior art attempts with the use of low-frequency and pulse-burst high-frequency currents for the treatment of muscle tissue have not been successful in providing certain desirable stimulation of the nerve and muscle systems. In accordance with the present invention, it has been found that high-frequency stimulations provide effects to the peripheral nervous system which are unattainable with the low-frequency stimulations of the prior art. More specifically, at high frequencies, the firing threshold of the peripheral nerves are elevated which cannot be accomplished at the low frequencies. Additionally, at high frequencies, the firing level of the most sensitive neurofibers, primarily of the "C" fiber type, is very high. These effects are desirable in the treatment of certain pain and muscle conditions and can be effectively controlled with the high-frequency currents.

It has been determined, however, that in addition to the use of high frequency, the modulation of the high frequencies at lower frequencies is required to fall within a certain range to produce the desired physiological response for such conditions as analgesia. It has been found that gating to produce the desired nerve effect should be in the range of 0.1 Hz to 200 Hz. If this frequency is maintained with a duty cycle of from 10% to 90%, the desired physiological response will be produced. Typically, the duty cycle should be selected to be in the range of 20% to 50% as the optimum for producing the appropriate nerve stimulation. For muscle stimulation it has been found that the on/off times of the high-frequency pulses are generally most desirable when alternated for predetermined periods of 0.1 second to 100 seconds.

In addition to the above application of the high-frequency currents for specific on/off time periods, it has been found that it is beneficial to vary the amplitude of the high-frequency stimulating signal by a signal to control its initial and terminal portions. Thus it has been found that a ramp function can be used to modulate the pulse amplitude to form initial and terminal ramp portions which vary from 0.5% to 50% of the total on-time of the pulse. This will produce an amplitude variation at the beginning and terminal portions of the high-frequency waveform which is desirable for providing the appropriate nerve and muscle stimulation. When combined with the gating of the high-frequency signal, the ramp function produces an effective output waveform for accomplishing particular effects in nerve and muscle tissue.

Turning now to FIG. 1a, a waveform is shown which is used in accordance with the present invention. The waveform is generally shown as a sinusoidal pulse train, having positive and negative portions and having a frequency which falls in the range of 500 Hz to 100,000 Hz. This signal can be provided by a pulse generator 12 as more particularly shown in FIG. 2. The generator 12, which may be of conventional construction, is designed to have a variable control 12a which is capable of varying the frequency within the noted range of 500 to 100,000 Hz.

Referring now to FIG. 1b, there is shown a square waveform which is used to control the application of the high-frequency pulse train to the body of a patient or other human or animal tissue for tissue stimulation. In FIG. 2, this control is exercised by gate control 18 coupled to control gate 16 which receives the output from pulse generator 12. The output of the gate 16 is coupled to an output amplifier 14 having a variable control 14a which sets a predetermined output magnitude of the high-frequency pulse train from pulse generator 12. The gate control 18 has adjusting elements 18a and 18b which are designed to control the square wave periods representing on and off times $T_a$ and $T_b$ respectively.

The gate control 18 may comprise any conventional circuitry which provides the square wave switching signal to open and close the gate 16 so that the time periods $T_a$ and $T_b$ represent alternate periods of transmission and non-transmission termination of the pulses from generator 12. The operation of the gate control 18 produces a series of pulse bursts of the high frequency shown in FIG. 1a for time periods of $T_a$ which are separated by periods of $T_b$ where no high-frequency signal is provided at the output of gate 16.

The output from the gate 16 is provided through output amplifier 14 to provide an amplified output of the gated signal to the electrodes 13 affixed to living tissue. The output from the electrodes 13 will thus be an amplified version of the pulse train signal provided by pulse generator 12 as controlled by gate 16. The output amplifier 14 may be a conventional structure capable of providing amplification of the pulses from generator 12 and having a control 14a for adjusting the amplitude level. Such structures are well-known in the art and therefore will not be described further since the particular structure does not form a part of the present invention.

As previously noted, it is also desirable to provide an amplitude modulation and control of the high-frequency pulse train during the initial and terminal portions of the intervals when it is provided at the output electrodes 13. Referring now to FIG. 1c, a ramp function is shown which is generated by ramp generator 20 in FIG. 2 for controlling the initial and terminal portions of the high-frequency pulse train signal. The ramp generator 20 can be of any conventional construction and is coupled to receive signals from the gate control 18 representing the time of initiation of the gating signal and the length of time that the gating signal will remain on. These signals, when coupled to the ramp generator, enable the ramp generator to generate an increasing ramp function having a period T1 starting at the beginning of the gating interval $T_a$ and ending at a time wherein T1 is equal to 0.5% to 50% of the on-time $T_a$ fixed by control 18a. The ramp generator is also constructed to provide a decreasing ramp function having a time period T2 wherein the time period T2 is equal to 0.5% to 50% of the on-time $T_a$ fixed by control 18a. The slope or period of the ramp can be changed by control 20a.

The output of ramp generator 20 is in turn connected to output amplifier 14 so the amplitude of the output high-frequency pulse train signal from pulse generator 12 goes from zero at the beginning of the interval $T_a$ to a predetermined level fixed by amplifier 14 after time period T1 and from that fixed predetermined level to 0 amplitude output at the termination of the interval $T_a$ during time period T2.

Referring now to FIG. 1d, the pulse train output from the electrodes 13 is shown as provided under the control of ramp generator 20, gate 16 and gate control 18. The high-frequency pulse train has an increasing amplitude at the beginning of each interval $T_a$ for the period T1 and then levels off to a value set by output amplifier 14 until the amplitude decreases during time period T2 to the termination of the interval $T_a$. This waveform represents that provided for the time period $T_a$ fixed by the on-time control 18a of the gate control 18. The output signal from the electrodes 13 is maintained at 0 by gate 16 during the period $T_b$ as controlled by off-time control 18b of gate control 18. The square wave control of gate 16 is repetitive so that the on-time intervals and off-time intervals cyclically alternate in accordance with the gate control 18.

As was previously noted, the gate control is fixed to produce on/off intervals of 0.1 second to 100 seconds for muscle stimulation and frequencies from 0.1 Hz to 200 Hz with duty cycles of 10% to 90% for nerve stimulation. In order to provide the appropriate frequency modulation for stimulation, the burst width control 22 is employed which provides the frequency modulation over the range of 0.1 to 200 Hz at 10% to 90% duty cycles. This control 22 then provides a control of gate 18 so that the on period $T_a$ (burst width) changes over a specific repetition period. By way of example, the control 22 can be a sweep generator structure or other conventional electronic control which will provide selective increases in the time period $T_a$ for a given number of repetitions and then repeat the same repetitions cyclically. The repetitions may be selected at any suitable number, for example 10, so long as the modulation is made within the range of 0.1 to 200 Hz to produce the varying periods of $T_a$. The control 22 cyclically repeats the pattern of variable width periods to establish an effective treatment. The same control 22 may be used to vary the pulse periods in the range of on time periods of 0.1 to 100 seconds so that the width of each successive interval is changed and the pattern is cyclically repeated after a predetermined number of pulse intervals.

While the present invention has been described with respect to nerve and muscle stimulation of human patients, it is evident that the inventive principles are equally applicable to all animal tissue. In addition, it is evident that other forms of amplitude control during the initial and terminal portions of the pulse train could be used to accomplish other effects. Obviously many other modifications and variations of the invention are possible in light of the above teachings. It is therefore to be understood that within the scope of the appended claims, the invention may be practiced otherwise than as is specifically described.

I claim:

1. A method of providing electrical stimulation of tissue comprising:
   generating a continuous train of repetitive pulses having a frequency in the range of 500 Hz to 100,000 Hz;
   gating said pulse train to produce an output signal having intervals of continuous pulse train output alternated with intervals of no pulse train output in the frequency range of 0.1 to 200 Hz; and
   delivering said output signal through electrodes to a tissue treatment area, said sequence of intervals of the pulse train output signal having a width of each successive interval different than the preceding and successive intervals.

2. The method of claim 1 further comprising cyclically repeating the sequence.

3. The method of claim 1 comprising frequency modulating the width of the intervals at 0.1 to 200 Hz at duty cycles of 10% to 90%.

4. The method of claim 1 wherein the step of gating said pulse train includes providing said pulse train with duty cycles of 10% to 90%.

5. The method of claim 1 wherein the step of generating said pulses includes generating the train of pulse having a frequency in the range of 1,000 Hz to 100,000 Hz.

6. The method of claim 1 wherein the step of generating said pulses includes generating the train of pulses having a frequency in the range of 3,500 Hz to 10,000 Hz.

7. The method of claim 1 wherein the pulse train comprises a sine wave and the gating is controlled by a square wave.

8. The method of claim 1 wherein said gating step includes gating the pulse train at frequencies of 1 Hz to 10 Hz.

9. The method of claim 1 wherein said gating step includes gating said pulse train at a frequency of 10 Hz to 200 Hz.

10. The method of claim 1 wherein said gating step includes gating said pulse train with duty cycles of 20% to 50%.

11. The method of claim 1 further including the step of varying the output signal amplitude of said pulse train.

12. The method of claim 11 wherein said step of varying the output signal amplitude of the pulse train includes varying the amplitude at the initial and terminal portions of the pulse train output interval in accordance with a ramp function.

13. The method of claim 11 wherein said step of varying the output signal amplitude of the pulse train includes varying the amplitude at the initial and terminal portions of the pulse train output interval in accordance with a ramp function, said ramp function increasing and decreasing the pulse train amplitude for a period in the range of 0.5% to 50% of the pulse train output interval.

14. The method of claim 1 wherein said pulses have a frequency in the range of 4,000 Hz to 100,000 Hz.

15. The method of claim 1 wherein the successive intervals comprise selectively increased intervals.

16. The method of claim 1 wherein the successive intervals comprise selectively increased intervals, with the selective increases being cyclically repeated.

17. The method of claim 1 wherein the successive intervals comprise selectively increased intervals, with the selective increases being cyclically repeated after a predetermined number of pulse intervals.

18. A method of providing electrical stimulation of tissue comprising:
   generating a continuous train of repetitive pulses having a frequency in the range of 500 Hz to 100,000 Hz;
   gating said pulse train to produce an output signal having intervals of continuous pulse train output alternated with intervals of no pulse train output in the frequency range of 0.1 to 200 Hz; and
   delivering said output signal through electrodes to a tissue treatment area, said sequence of intervals of the pulse train output signal having a width of each successive interval different from the preceding and successive intervals, said intervals having a duration in the range of 1 second to 100 seconds.

19. The method of claim 18 wherein the step of generating includes generating a pulse train in the frequency range of 1,000 Hz to 100,000 Hz.

20. The method of claim 19 wherein the step of generating includes generating a pulse train in the range of 3,500 Hz to 10,000 Hz.

21. The method of claim 18 wherein said pulse train is a sine wave and the gating is controlled by a square wave.

22. The method of claim 18 further including the step of varying the output signal of the pulse train.

23. The method of claim 18 further including the step of varying the output signal of the pulse train comprising varying the pulse train amplitude from 0 to a predetermined value during the initial portion of the pulse train output interval and varying the amplitude from that predetermined value to 0 at the terminal portion of the pulse train output interval.

24. The method of claim 23 wherein the amplitude is varied by a ramp function.

25. The method of claim 23 further comprising controlling the periods of increase and decrease of said amplitude to have a period corresponding to 0.5% to 50% of the output signal interval.

* * * * *